United States Patent [19]

Abraham, II

[11] Patent Number: 4,979,516
[45] Date of Patent: Dec. 25, 1990

[54] PRESSURE SENSITIVE MOUTH PIECE

[76] Inventor: James G. Abraham, II, 3675 Pecos McLeod, Ste. 700, Las Vegas, Nev. 89121

[21] Appl. No.: 331,605

[22] Filed: Mar. 30, 1989

[51] Int. Cl.⁵ .............................................. A61B 5/10
[52] U.S. Cl. .................................. 128/777; 128/862; 433/229
[58] Field of Search ............... 128/359, 774, 776, 777, 128/782, 859, 861, 862; 433/6, 68, 69, 229; 606/234 (U.S. Only), 235 (U.S. Only)

[56] References Cited

U.S. PATENT DOCUMENTS

| 4,041,937 | 8/1977 | Diaz | 128/15 |
| 4,178,589 | 12/1979 | Nunn et al. | 340/573 |
| 4,390,028 | 6/1983 | Okano et al. | 128/777 |
| 4,402,326 | 9/1983 | Okano et al. | 128/774 |
| 4,488,873 | 12/1984 | Bloomfield et al. | 433/71 |
| 4,521,186 | 6/1985 | Wodlinger et al. | 433/71 |
| 4,593,686 | 5/1986 | Lloyd et al. | 128/136 |
| 4,629,424 | 12/1986 | Lauks et al. | 433/6 |
| 4,842,519 | 6/1989 | Dworkin | 128/777 |

Primary Examiner—Randall L. Green
Assistant Examiner—Randy Shay
Attorney, Agent, or Firm—Quirk, Tratos & Roethel

[57] ABSTRACT

A pressure sensitive mouth piece has a pressure detector-sound unit assembly mounted on or embedded in the molded bite guard. When a patient clenches or bruxes his teeth, the pressure detector senses that condition and activates the sound unit to emit a tone audible to the patient. The patient is thereby alerted that he is clenching or bruxing his teeth so he can stop. Alternatively, a mechanical clicker can be embedded in the mouth piece and will emit an audible tone when the patient clenches or bruxes his teeth.

28 Claims, 3 Drawing Sheets

PRESSURE SENSITIVE MOUTH PIECE

BACKGROUND OF THE INVENTION

The invention relates to a pressure sensitive mouth piece and more particularly to a pressure sensitive mouth piece that emits audible tones or other sensory stimuli to alert the wearer that he is grinding his teeth.

One of the destructive tendencies that people have with regard to their teeth is a tendency to unconsciously clench or brux their teeth, especially while they sleep. This clenching or bruxing action is damaging, not only to the teeth themselves, but also to the supporting structure of the teeth (both the hard, bony material and the soft tissue) in the mouth. Patients who have this tendency suffer headaches, sore jaws, and stiff necks, not to mention the potentially severe damage to their teeth and supporting structure.

The conventional solution is for a dentist to custom fit a bite guard that is worn over either the upper or lower teeth. The bite guard is molded from a plastic material after the dentist makes an impression of the patient's teeth. However, the bite guard does not actually prevent the patient from grinding his teeth. All the bite guard does is act as a physical separation between the patient's upper and lower teeth, When the patient clenches or bruxes his teeth, the teeth grind on the surface of the bite guard rather than directly, on the opposed teeth.

It is an object of the present invention to provide a pressure sensitive mouth piece that not only provides a physical separation between the patient's upper teeth and lower teeth but also emits an audible tone to alert the patient whenever he engages in the act of clenching or bruxing his teeth.

It is a feature of the present invention that a mouth piece is comprised of a bite guard with a sensing unit that involves a pressure detector that is activated by the act of the patient clenching or bruxing his teeth. The activation of the pressure detector closes a circuit which sends current from a battery to an integrated circuit which causes an audible tone to be emitted from a speaker thereby alerting the patient that teeth clenching or bruxing is occurring. The patient then becomes aware that he is clenching or bruxing and he can consciously retrain himself to stop. The pressure detector, battery, integrated circuit and speaker are all mounted on or incorporated into the bite guard to be worn inside the patient's mouth.

It is another feature of the present invention that a mouth piece is comprised of a bite guard and a mechanical "clicker" that emits mechanically an audible signal when a patient clenches or bruxes his teeth.

It is an advantage of the present invention that, when the patient begins to grind his teeth, an audible signal is emitted from a location quite close to the patient's ear. This signal will alert the patient that he is grinding his teeth, even if such teeth grinding were being done subconsciously by the patient. If the teeth grinding is being done while the patient is asleep, the audible tone will be loud enough to awaken the patient so he can stop grinding his teeth.

SUMMARY OF THE INVENTION

A pressure sensitive mouth piece comprises a plastic or rubber bite guard in which is implanted a pressure detector. The pressure detector is connected by wire to a sound unit also implanted in the bite guard. The sound unit comprises an integrated circuit, a speaker and a battery. When the patient grinds his teeth, the pressure detector senses this condition and an electronic circuit is activated. Power from the battery activates the integrated circuit which causes an audible tone to be emitted from the speaker. The patient detects the audible tone which thereby alerts the patient that he is grinding his teeth.

Alternatively, a mechanical member is implanted in the bite guard. Upon the patient clenching or bruxing, the mechanical member is deformed and emits an audible sound that is detected by the patient.

DESCRIPTION OF THE PREFERRED EMBODIMENTS

Figure 1:
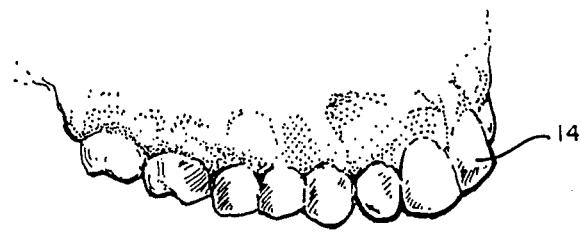
FIG. 1 depicts in perspective the upper teeth of a patient and the pressure sensitive mouth piece of the present invention.

The pressure sensitive mouth piece of the present invention is shown generally at 10 in FIG. 1. A conventional bite guard 12 is formed of rubber or plastic by any well known methods. The bite guard 12 may be custom made to correspond to the upper or lower teeth pattern 14 of the patient. If a patient cannot wear a full bite guard, a partial bite guard that conforms to only a portion of the patient's upper or lower teeth pattern can also be used. Alternatively, a non-custom bite guard can also be used in the event the patient does not wish to incur the extra expense of a customized bite guard. During the manufacturing process for the bite guard 12, a sound unit 20, a pressure detector 30 and connecting wires 40 are embedded into the bite guard 12.

Figure 3:
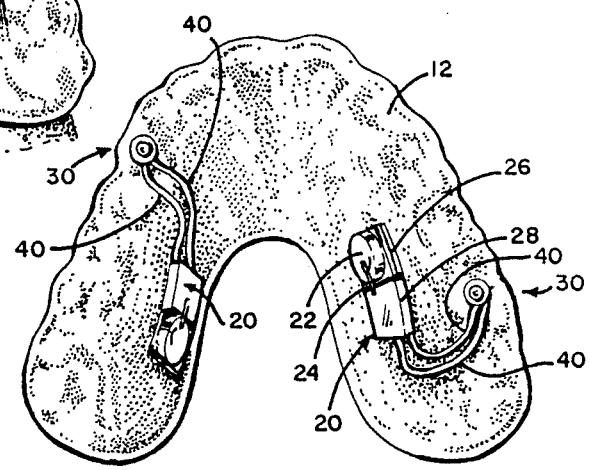
FIG. 3 is a bottom view of an alternate embodiment of the pressure sensitive mouth piece of the present invention.
Figure 4:
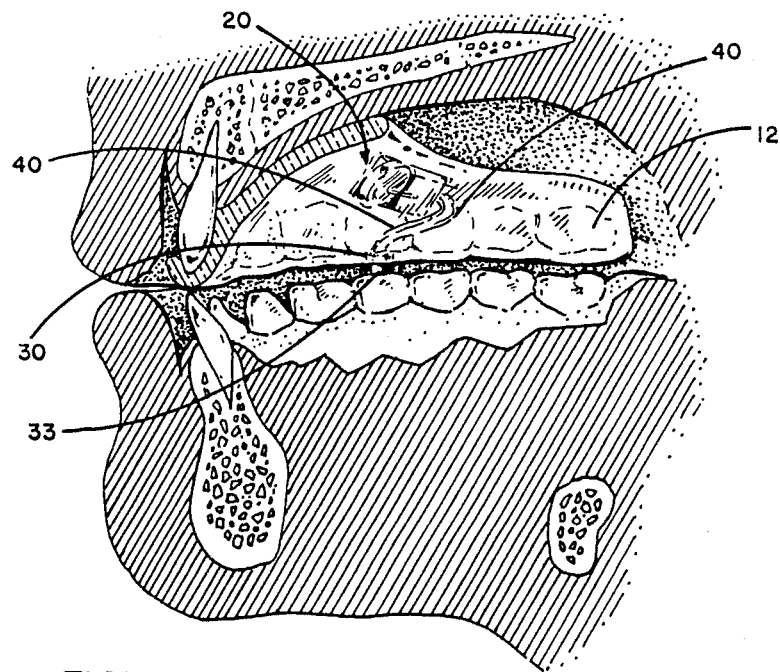
FIG. 4 is a side view in section that shows the pressure sensitive mouth piece of the present invention in use in the patient's mouth.

FIG. 3 shows an alternate embodiment in which the sound unit 20, the pressure detector 30 and the connecting wires 40 are merely attached to the interior surface of the bite guard 12 rather than embedded in the material of the bite guard. This alternate embodiment permits replacement of any parts that may become inoperable.

The sound unit 20 comprises a power supply means 22, an integrated circuit means 26 and a speaker means 28. In the preferred embodiment, the power supply means 22 is a battery, typically a 1.5 volt circular model used in small calculators or watches. The battery 22 is mounted to the integrated circuit means 26 and held in place by a spring clamp 24. The integrated circuit means 26 is mounted next to a speaker means 28. The speaker is preferably a piezo-electric speaker, but other appropriate speakers may be used.

Figure 5:
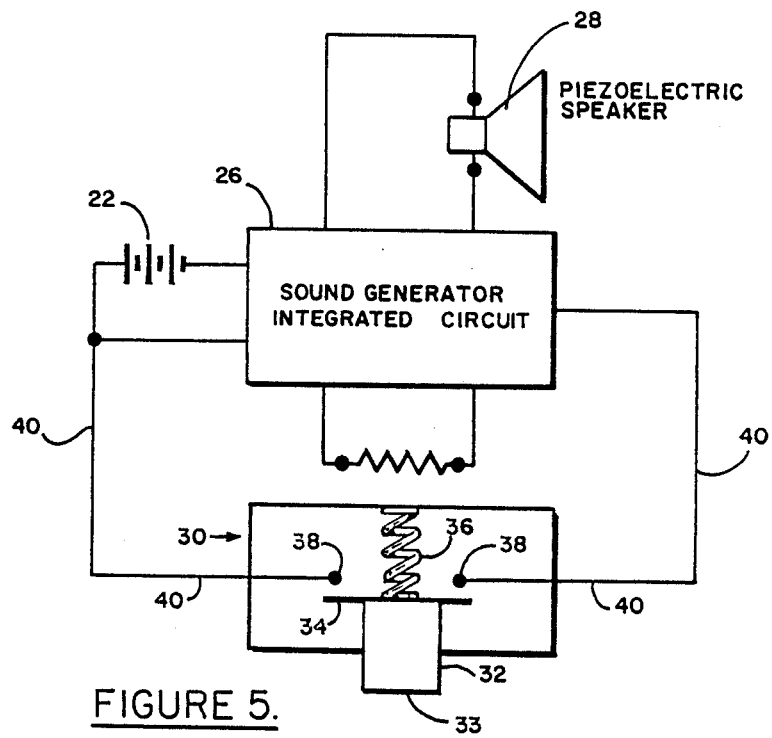
FIG. 5 is a wiring schematic of the pressure switchsound unit of the present invention.

The pressure detector means 30, in the preferred embodiment, is a piston-type switch shown in detail as a part of the schematic in FIG. 5. The upper portion of the pressure detector 30 is a cylindrical housing 31 into which are attached the ends 38 of each connecting wire 40. Mounted within the cylindrical housing 31 is a T-shaped piston 32. The upper portion of the piston 32 is a conductive metal plate 34. The lower portion of the piston 32 is a rod member 33. A spring 36 acts to bias the rod member 33 out of the cylindrical housing 31 so that the conductive metal plate 34 is normally not in contact with the ends 38 of the connecting wires 40 so that the electronic circuit remains open.

Figure 2:
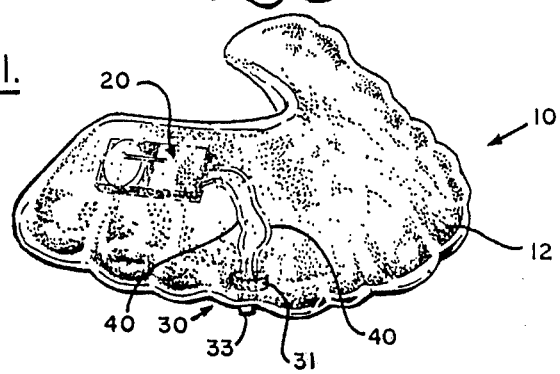
FIG. 2 is a bottom view of the pressure sensitive mouth piece of the present invention mounted in the patient's mouth.
Figure 2:
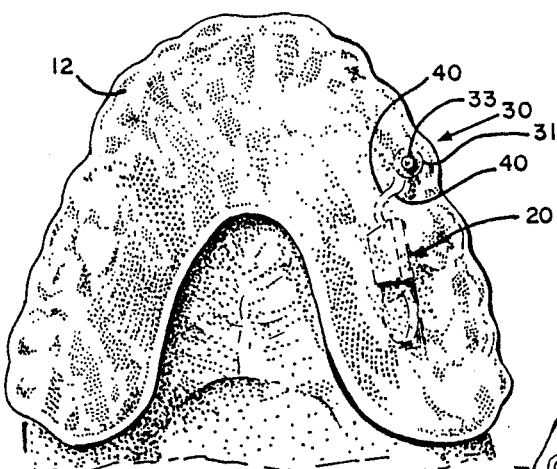

As shown in FIGS. 1 and 2, the rod member 33 extends through the surface of the bite guard 12 through an aperture in the bite guard 12 provided in the manufacturing process during the embedding of the sound unit 20, the pressure detector 30 and the connecting wires 40 in the bite guard 12. During the act of the patient clenching or bruxing his teeth, the patient's lower teeth will contact the rod member 33 and push it up against the action of the spring 36 in the cylindrical housing 31. This upper movement will cause the conductive metal plate 34 to contact the ends 38 of the connecting wires 40 to complete the electronic circuit. Current from the batter 22 will flow into the integrated circuit 26 which then activates the speaker 28 to emit an audible tone.

The sound unit 20 comprising the battery 22—integrated circuit 26—speaker 28 is a conventional assembly that is available from Western Trimming Corp., Chatsworth, Calif. 91311. It is also available from Leo Chen, 75 Robinhood Drive, San Francisco, Calif. 94127.

With the speaker being placed in the oral cavity of the patient, the sound is transmitted through the bone structure of the patient's mouth to the nearby ears of the patient. The volume of the speaker, therefore, can be quite low and still be readily audible to the patient, while being low enough that a person in proximity to the patient will not hear the tone. The tone should be loud enough, however, to awaken the average sleeper so that he can cease the grinding of this teeth.

As shown in FIG. 3, a plunger-speaker unit can be disposed on each lateral area of a bite guard in case the patient only clenches or bruxes his teeth on one side of his mouth or if the patient clinches or bruxes his teeth on alternate sides of his mouth.

Figure 6:
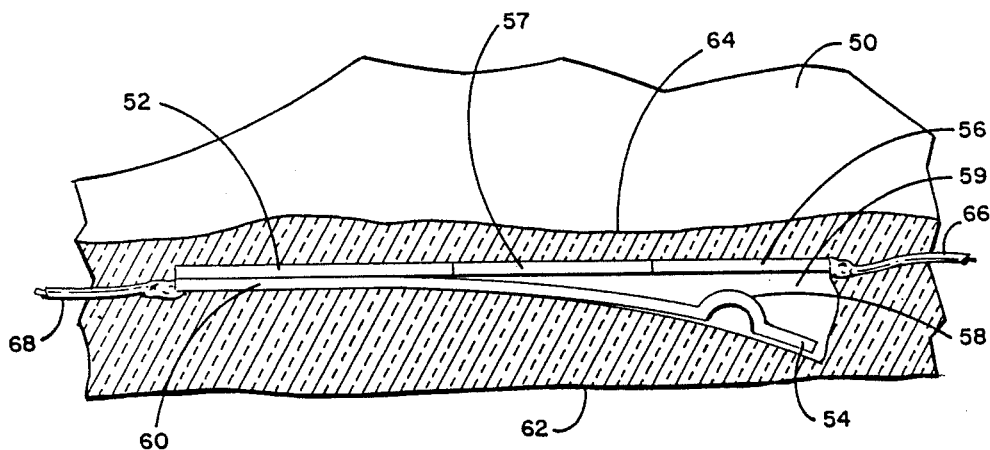
FIG. 6 shows the details of an alternate pressure detector switch of the present invention.

FIG. 6 shows an alternate embodiment of the present invention in which the entire pressure detector is embedded within the bite guard. This embodiment utilizes a spring-type switch 60 instead of a piston-type switch. As shown in FIG. 6, the top edge 64 of the bite guard 62 is formed to conform to the pattern of the patient's teeth 50. During fabrication of the bite guard, the sound unit (not shown) along with the connecting wires 66, 68 and the spring-type switch 60 are all embedded in the bite guard 62. A hollow chamber 59 is also provided to allow for the necessary movement of the spring switch 60. Connecting wire 68 is attached to the spring switch base 52 and the spring switch arm 54. The other connecting wire 66 is attached to the spring switch contact member 56. Switch base 52 and contact member 56 are electrically separated by an insulator 57. The spring switch arm 54 is a curved member that is normally biased away from contact member 54. When a patient clenches or bruxes, the bite guard 62 deforms causing contact point 58 on switch arm 54 to touch contact member 56. This completes the circuit between connecting wire 68 and connecting wire 66 allowing current to flow from the power supply to the integrated circuit to cause an audible tone to be emitted from the speaker. When the patient stops clenching or bruxing, the switch arm 54 will separate from contact member 56 and the audible tone will cease.

Figure 7:
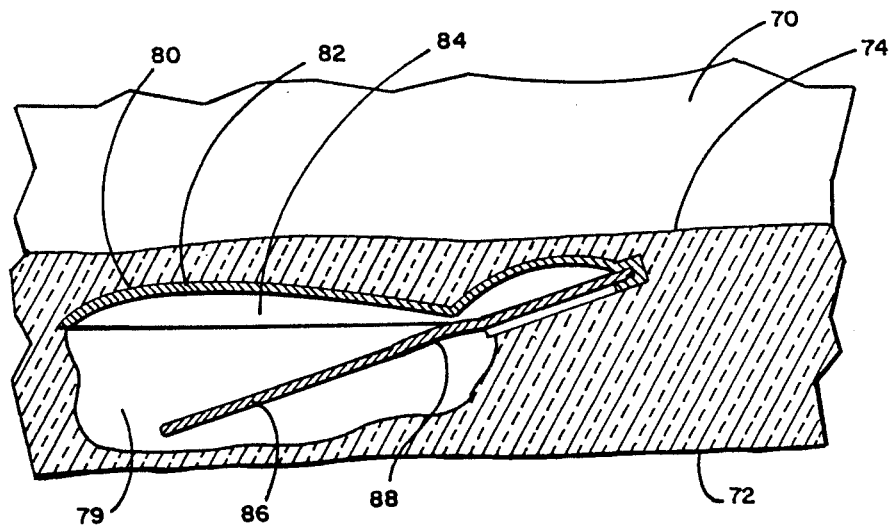
FIG. 7 shows the details of a mechanical "clicker" of the present invention.

FIG. 7 shows another embodiment of the present invention wherein the audible tone is made by a mechanical member only. In this embodiment, no electrical circuitry is required; there is no power supply, no speaker, no integrated circuit and no connecting wires. In this embodiment, the top edge 74 of the bite guard 72 is made to conform to the pattern of the patient's teeth 70. During fabrication of the bite guard, a hollow chamber 79 is provided in which is included a pressure detector in the form of a mechanical member 80 that will act as a "clicker" when the patient clenches or bruxes his teeth. The mechanical member 80 can be a conventional "clicker" normally found in games played in the home, e.g., Jeopardy ® manufactured by Pressman Toy Corp., New York, N.Y.

The mechanical member 80 is preferably fabricated from spring steel sheet. The mechanical member 80 comprises a fixed upper arm 82 joined at one end to the movable lower arm 86. The upper arm 82 is slightly concave to provide a sound chamber. The lower arm 86 has a slightly curved bend point 88.

When a patient clenches or bruxes his teeth, the bite guard 72 is deformed which causes the lower arm 86 to pivot toward the upper arm 82. During this pivoting movement, the movable lower arm flexes about the bend point 88 causing an audible "click" to occur. This "click" is amplified by the concave sound chamber 82 and is loud enough to be heard by the patient. This alerts the patient that he is clenching or bruxing.

Various modifications can be made to the basic invention. The piston-type switch can be completely embedded in the bite guard and would be activated by the patient's teeth pressing on the flexible bite guard causing the rod member to move against the action of the spring to complete the circuit. Similarly, the spring-type switch or the mechanical member can be directly exposed to the patient's teeth rather than completely embedded in the bite guard. Finally, either the electronic assembly or the mechanical member can be utilized in a bite guard that is designed to be worn on the patient's lower teeth rather than his upper teeth. Accordingly, the invention should not be limited by the foregoing description, but rather should be defined only by the following claims.

I claim:
1. A pressure sensitive mouth piece comprising:
   (a) a premolded bite guard means to be worn between a patient's upper and lower teeth for preventing contact between the patient's upper and lower teeth; and
   (b) means attached to the bite guard means and directly responsive to pressure from the patient's teeth for emitting a tone audible to the patient when the patient grinds his teeth and exerts pressure on the bit guard.
2. The pressure sensitive mouth piece of claim 1 wherein the bit guard means is plastic.
3. The pressure sensitive mouth piece of claim 1 wherein the bite guard means is rubber.
4. The pressure sensitive mouth piece of claim 1 wherein the means for emitting a tone comprises:

(a) a pressure detector; and (b) a sound unit connected to the pressure detector whereby when a patient grinds his teeth the pressure detector is activated to effect the audible tone to emit from the sound unit.

5. The pressure sensitive bite guard of claim 4 wherein the sound unit comprises:

(a) a speaker means;

(b) an integrated circuit means for activating the speaker means; and (c) a power supply means for powering the integrated circuit means.

6. The pressure sensitive mouth piece of claim 4 wherein the pressure detector and the sound unit are each attached to a surface of the bite guard.

7. The pressure sensitive bite guard of claim 4 wherein the pressure detector and the sound unit are each embedded within the bite guard.

8. A pressure sensitive mouth piece comprising:

(a) a bite guard adapted to be worn over a patient's teeth, and (b) a pressure detector embedded in the bite guard, (c) a pressure detector comprising a mechanical member having a fixed upper arm joined to a movable lower arm, said movable lower arm having a bend point whereby when the patient clenches or bruxes, the movable lower arm flexes about the bend causing an audible click that can be detected by the patient.

9. The pressure sensitive mouth piece of claim 8 wherein the fixed upper arm is slightly concave to provide a sound chamber whereby the audible click is amplified.

10. A pressure sensitive mouth piece comprising:

(a) a bite guard means to be worn between a patient's upper and lower teeth for preventing contact between the patient's upper and lower teeth;

(b) a pressure detector attached to the bite guard means; and (c) a sound unit attached to the bite guard means and connected to the pressure detector whereby when a patient clenches or bruxes his teeth the pressure detector senses that condition and activates the sound unit to emit an audible tone which is perceptible to the patient.

11. The pressure sensitive mouth piece of claim 10 wherein the bite guard means is made of plastic.

12. The pressure sensitive mouth piece of claim 10 wherein the bite guard means is made of rubber.

13. The pressure sensitive mouth piece of claim 10 wherein the sound unit is embedded within the bite guard means.

14. The pressure sensitive mouth piece of claim 10 wherein the sound unit is attached to the surface of the bite guard means.

15. The pressure sensitive mouth piece of claim 10 wherein a plurality of sound units and pressure detectors are disposed within the bite guard means.

16. The pressure sensitive mouth piece of claim 15 wherein a sound unit and a pressure detector are disposed in each lateral area of the bite guard means.

17. The pressure sensitive mouth piece of claim 10 wherein the pressure detector is a piston-type switch.

18. The pressure sensitive mouth piece of claim 17 wherein the piston-type switch comprises:

(a) a cylindrical housing, (b) a rod member movably mounted in the cylindrical housing, (c) spring means associated with the rod member whereby the rod member is biased to extend from the cylindrical housing, and (d) a metal plate carried by the rod member whereby when the switch is closed the sound unit is activated.

19. The pressure sensitive mouth piece of claim 10 wherein the sound unit is connected to the pressure detector by means of connector wires.

20. The pressure sensitive mouth piece of claim 10 wherein the sound unit includes a speaker means.

21. The pressure sensitive mouth piece of claim 20 wherein the sound unit further includes an integrated circuit means connected to the speaker means whereby the audible tone is emitted by the speaker means when the integrated circuit means is activated.

22. The pressure sensitive mouth piece of claim 21 wherein the sound unit further includes a power supply means.

23. The pressure sensitive mouth piece of claim 22 wherein the power supply means is a battery.

24. The pressure sensitive mouth piece of claim 23 wherein the battery is a 1.5 volt circular battery.

25. The pressure sensitive mouth piece of claim 10 wherein the pressure detector is spring a switch.

26. The pressure sensitive mouth piece of claim 25 wherein the spring switch comprises:

(a) a switch base, (b) a switch arm connected to the switch base, said switch arm including a contact point therein, and (c) a contact member insulated from the switch base whereby when the switch is closed, the sound unit is activated.

27. The pressure sensitive mouth piece of claim 10 wherein the sound unit comprises a power supply means, an integrated circuit means connected to the power supply means and a speaker means connected to the integrated circuit means.

28. The pressure sensitive mouth piece of claim 27 wherein the power supply means is a battery and the speaker means is a piezoelectric speaker.

* * * * *